United States Patent [19]
Yadan et al.

[11] Patent Number: 5,817,520
[45] Date of Patent: Oct. 6, 1998

[54] SPECTROPHOTOMETRIC METHODS FOR ASSAYING TOTAL MERCAPTANS, REDUCED GLUTATHIONE (GSH) AND MERCAPTANS OTHER THAN GSH IN AN AQUEOUS MEDIUM REAGENTS AND KITS FOR IMPLEMENTING SAME

[75] Inventors: Jean-Claude Yomtob Yadan, Paris; Marc Gabriel Antoine, Champs sur Marne; Jean Raymond Chaudiere, St Maur Des Fosses, all of France

[73] Assignee: Oxis International S.A., Bonneuil-sur-Marne, France

[21] Appl. No.: 695,705

[22] Filed: Aug. 12, 1996

(Under 37 CFR 1.47)

Related U.S. Application Data

[63] Continuation of Ser. No. 256,014, filed as PCT/FR92/01184 Dec. 15, 1992 published as WO93/13071 Jul. 8, 1993, abandoned.

[30] Foreign Application Priority Data

Dec. 20, 1991 [FR] France .................................. 91 15868

[51] Int. Cl.$^6$ ........................................................ G01N 33/00
[52] U.S. Cl. ........................ 436/120; 430/119; 430/166; 422/61; 546/152; 546/179; 546/180
[58] Field of Search .................................... 436/119, 120, 436/166; 546/152, 153, 173, 179, 180; 422/61

[56] References Cited

U.S. PATENT DOCUMENTS

| | | | |
|---|---|---|---|
| 2,940,974 | 6/1960 | Surrey | 523/212 |
| 3,002,001 | 9/1961 | Surrey | 546/159 |
| 3,755,332 | 8/1973 | Wasley et al. | |
| 3,819,374 | 6/1974 | Kemp | 430/12 |
| 4,058,613 | 11/1977 | Abbruzzese et al. | 514/311 |
| 4,282,219 | 8/1981 | Hannah | 514/201 |
| 4,431,774 | 2/1984 | Felder-Schraner et al. | 522/15 |
| 4,678,781 | 7/1987 | Jung | 514/200 |

FOREIGN PATENT DOCUMENTS

| | | |
|---|---|---|
| 781812 | 5/1935 | France . |
| 1172432 | 2/1959 | France . |
| 2214051 | 10/1972 | Germany . |
| 61-258268 | 11/1986 | Japan . |

OTHER PUBLICATIONS

F. Tietze *Anal. Biochem.* 1969, 27, 502–522.
B. L. Ling et al, *J. Chromatogr.* 1991, 553, 433–439.
E. Sofic et al *Fresenius J. Anal. Chem.* 1991, 339, 258–260.
G. L. Ellman *Arch. Biochem. Biophys.* 1959, 82, 70–77.
J. Sedlak et al. *Anal. Biochem.* 1968, 25, 192–205.
N. P. Luthra et al. *Anal. Biochem.* 1981, 117, 94–102.
M. W. Fariss et al. *Method. Enzymol.* 1987, 143, 101–109.
G. C. Rice et al, *Cancer Res.* 1986, 46, 6105–6110.
E. M. Kosower et al, in "The Functions of Glutathione: Biochemical, Physiological, Toxicolgical & Clinical Aspects" A Larssen et al. ed, Raven Press; New York, 1983, pp. 243–250.
C. J. Holloway *J. Chromatogr.* 1987, 390, 101–110.
B. Mutus et al. *Anal. Biochem.* 1989, 177, 237–243.
O. W. Griffith *Anal. Biochem.* 1980, 106, 207–212.
P. J. Hissim et al. *Anal. Biochem.* 1976, 74, 214–226.
J. Martensson *J. Chromatogr.* 1987, 420, 152–157.
B. L. Ling et al. *Anal. Chim. Acta* 1989, 227, 203–209.
M. Inoue et al, *J. Protein Chem.* 1987, 6, 207–225.
C. J. Cooksey et al. *J. Chem. Soc (B)* 1968 1191–1197.
G. B. Barlin et al. *J. Chem. Soc. Perkin Frans. II* 1975, 298–302.
K. Matsumura *J. Am. Chem. Soc.* 1927, 49, 810–818.
F. Pirrone et al. *Chem. Abstr.* 1936, 30, 2194.
E. Moness et al. *Chem. Abstr.* 1936, 30, 5726.
R. F. Lutz et al. *J. Am. Chem. Soc.* 1946, 68, 1324–1325.
E. Pouterman et al. *Experientia* 1947, 3, 28.
R. H. Baker et al. *J. Am. Chem. Soc.* 1947, 69, 704–705.
W. H. Rueggeberg et al. *J. Am. Chem. Soc.* 1947, 69, 1222–1223.
A. R. Surrey et al. *J. Am. Chem. Soc.* 1959, 81, 2894–2897.
M. Tomita et al. *Chem. Abstr,* 1953, 47, 3314e.
T. Ueda et al. *Chem. Abstr.* 1955, 49, 10957a.
R. U. Schock *J. Am. Chem. Soc.* 1957, 79, 1670–1672.
H. Vogt et al. *Chem. Abstr,* 1958, 52, 16695a.
A. Rieche et al, *Chem. Ber,* 1959, 92, 2239–2252.
I. S. Ioffe et al. *J. Gen. Chem. USSR* 1960, 30,95–97.

(List continued on next page.)

*Primary Examiner*—Arlen Soderquist
*Attorney, Agent, or Firm*—Jacobson, Price, Holman & Stern, PLLC

[57] ABSTRACT

According to the invention, the total mercaptans in an aqueous sample are assayed by means of the formation of a chromophoric substitution product between all the mercaptans present in the sample and a reagent corresponding to the general formula I:

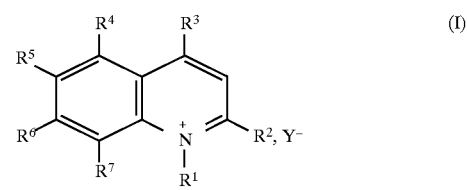

Reduced glutathione (GSH) is assayed in the form of a chromophoric thione formed specifically by alkalization from the substitution product formed above between GSH and the reagent.

The concentration of mercaptans distinct from GSH is obtained by subtraction of the concentrations obtained in the preceding assays.

Application to the assay of mercaptans and GSH, especially in the presence of other mercaptans, in particular in biological media.

35 Claims, 3 Drawing Sheets

OTHER PUBLICATIONS

G. Illuminati et al. *J. Am. Chem. Soc.* 1967, 89, 3521–3524.

J. W. Bunting et al. *Can. J. Chem.* 1974, 52, 962–974.

G. B. Barlin et al. *J. Chem. Soc. Perkin Trans 2* 1975 1267–1270.

W. O. Foye et al. *J. Pharm. Sci.* 1979, 68, 336–338.

E. Bald *Talanta* 1980, 27, 281–282.

C. Rømming et al, *Acta. Chem. Scand. B* 1983, 37, 791–795.

P. J. Zavala et al. *Talanta* 1985, 32, 285–289.

Ling. B. Lin, Dewaele CL, Baeyens W.R.G. (1991) J. Chromatogr., 553(1–2), 433–9.

SPECTROPHOTOMETRIC METHODS FOR ASSAYING TOTAL MERCAPTANS, REDUCED GLUTATHIONE (GSH) AND MERCAPTANS OTHER THAN GSH IN AN AQUEOUS MEDIUM REAGENTS AND KITS FOR IMPLEMENTING SAME

This is a continuation of application Ser. No. 08/256,014, filed Jun. 20, 1994, now abandoned, which is a National Stage application of PCT/FR92/01184, filed Dec. 15, 1992 published as WO93/13071 jul. 8, 1993.

The invention relates to the assay of mercaptans and reduced glutathione, especially in biological media.

Its subject is more particularly a spectrophotometric process for assaying total mercaptans, reduced glutathione (abbreviated GSH) and, by subtraction, mercaptans other than GSH, in an aqueous, especially biological, medium, reagents and set or kits for implementing this process.

Glutathione, a ubiquitous compound, is a key molecule from the physiological point of view, because of its numerous biochemical functions (reference 1). Consequently, the variations in its concentration, in particular a decrease in its normal intracellular level (1–10 mM), can cause substantial disorders. It is therefore necessary to be able to have a method for assaying GSH which is reliable, simple, sensitive and specific for this biochemical parameter.

The existence of numerous methods for assaying GSH suggests that these methods are not satisfactory (reference 2).

The known techniques for measuring mercaptans in general, and GSH in particular, exploit either one of the two principal chemical properties of mercaptans: reducing power and nucleophilic power, hence their classification into:

Methods using the reducing power of mercaptans:

These methods are not specific for GSH, they therefore necessitate a chromatographic purification step in order to assay the GSH and, in some cases, the presence of a coupling enzyme such as for example glutathione reductase (reference 3); and Methods using the nucleophilic power of mercaptans:

These methods are based on the substitution of halogenated derivatives (for example of the dinitrohalobenzene or monohalobimane type) with or without glutathione transferase. These methods too are not specific for GSH in the absence of enzyme and necessitate a chromatographic separation step in order to assay the GSH.

Depending on the cases, the detection may be of the spectrophotometric, spectrofluorimetric (reference 4) or electrochemical (reference 5) type.

The following text will be limited to the methods using UV/visible absorption spectrophotometry or spectrofluorimetry as the technique for detection.

The methods using the reducing power of mercaptans are based on a thiol-disulphide exchange, according to the following reaction mechanism (in the case of glutathione):

2 GS$^-$+RSSR→GSSG+2 RS$^-$

The most widely known uses the ELLMAN reagent (references 6 and 7). This method, based on the formation of a chromophore at 412 nm, is not very complex, but the instability of the ELLMAN reagent towards light and pH (hydrolysis), and the auto-oxidation of the liberated chromophore necessitate the carrying-out of a reference measurement which renders the test cumbersome. All these make it an unusable reagent in Clinical Biology on large series of samples.

The selenized analogue of the ELLMAN reagent has been synthesized and used for assaying mercaptans (reference 8). It is more resistant than the ELLMAN reagent towards alkaline hydrolysis but has, otherwise, the same disadvantages as the latter.

Finally, the use of pyridine disulphides should be mentioned (reference 9).

Generally, the reagents for thiol-disulphide exchange cannot be used for a specific assay of GSH.

The methods based on the nucleophilic power of mercaptans exploit their capacity for addition onto electrophilic reagents, namely:

1° Activated haloaromatic reagents:

These reagents of the 1-chloro-2,4-dinitrobenzene (CDNB) or 2,4-dinitro-1-fluorobenzene (DNFB) type are not specific for the thiol groups at alkaline pH. They require the presence of an enzyme such as GSH transferase, whose activity they are, moreover, used to measure. The low sensitivity of these reagents is one of the major disadvantages of these methods. Furthermore, their non-enzymatic reactivity is not zero, which excludes an assay completely specific for GSH. In order to overcome this disadvantage, numerous methods are based on the chromatographic separation of the reaction products such as, for example, the high-performance liquid chromatography (HPLC) method of REED (references 10 and 11) which couples a formation of derivatives or derivatization, of amines (by means of DNFB : Sanger reagent) with an S-carboxymethylation, but which is long and cumbersome to implement.

2° Monohalobimanes (reference 12):

These compounds can react with nucleophilic groups other than thiol groups, such as for example amines. They too are not specific for GSH in the presence of other mercaptans: it is therefore, here also, necessary to integrate a chromatographic separation step into the procedure. This process makes it possible, nevertheless, to obtain an exhaustive profile of the mercaptans present. However, the photosensitivity of the reagents and the reaction products require precautions during use which render the assay method cumbersome.

Moreover, the slow kinetics of monochlorobimane, at a pH of less than or equal to 8, makes it possible to exploit the biochemical specificity of glutathion-S-transferases at near neutral pH. This reagent slowly penetrates into the intact cells, in which it reacts with the enzyme and its substrate, GSH, thereby permitting an assay by flow cytometry (reference 13). The monobromotrimethylammoniobimane derivative (reference 14) has, for its part, the advantage of a higher solubility in water and permits a conductimetric detection, but the latter is difficult to standardize.

Whatever their particular advantages, in a general manner, most of these methods require a sophisticated chromatographic separation, and their implementation is too long to permit rapid analysis of a large series of samples.

3° Iodoacetic acid derivatives:

These compounds have a lower specificity than the reagents mentioned above, their sensitivity is rather average, or even poor in certain cases. They are generally unstable to light and necessitate chromatographic separation because of their absorption characteristics which are similar to those of the addition product.

4° Maleimide derivatives:

The specificity of these compounds is not better than that of the preceding reagents. Their sensitivity is good only in the case where the addition product is fluorescent.

One of the major disadvantages of the latter method is that a decrease of pre-existing absorption is monitored, which is less reliable and more delicate than monitoring the increase of a new absorption.

5° Reagents possessing an activated electrophilic double bond (Michael acceptors):

These reagents include:

the enones (reference 15) which react very slowly with nitrogenous or oxygenated nucleophilic compounds, but more rapidly with sulphur-containing nucleophilic compounds; their specificity is never total towards thiol groups; their sensitivity, for its part, is variable according to the reagent considered; they generally exhibit the same major disadvantages as the preceding reagents;

vinylpyridines which are slow reagents, not very soluble in aqueous medium, and are used for blocking the SH group of mercaptans in general, and of glutathione (reference 16) in particular, but not for assaying it.

Two types of fluorescent reagents should finally be mentioned which are not suitable for a routine assay because of methodological complexity and a specificity which is limited with respect to thiol groups in general and is non-existent with respect to glutathione, they are:

ortho-phthalic aldehyde which requires the presence of a thiol group and a primary amine in order to yield a fluorescent isoindole derivative (references 17 and 18); and benzoxa-1,3-diazole derivatives, in particular 7-chloro-2-benzoxa-1,3-diazole-4-sulphonate (SBD-Cl) and 7-fluoro-2-benzoxa-1,3-diazole-4-sulphonate (SBD-F), which require a long reaction time and an alkaline pH of 9.5 (references 19 and 20).

The aim of the invention is to overcome the disadvantages of the known methods for assaying mercaptans in general and GSH in particular by providing:

calorimetric reagents specific for mercaptans in crude samples, especially biological samples, which are capable of permitting a specific assay of GSH in the presence of contaminating mercaptans, and which are rapid, that is to say whose total reaction time with the mercaptans in the medium is less than 15 minutes under the operating conditions;

a process for using such reagents permitting the assay, in a single sample, of the total mercaptans in a first step and reduced GSH in a second step, which would result in the determination of three physiological parameters:
the quantity of total mercaptans
the quantity of GSH
the quantity of mercaptans distinct from GSH, by subtraction.

The aim of the invention is, in particular, to develop a simple and rapid process for the measurement of reduced GSH, adapted to a routine assay on large series of samples, which involves:

the formation of a chromophore which absorbs most often in the visible, the measurement of whose absorbance does not require a specific spectrophotometer;

an end point and not a kinetic assay;

a short incubation time: for example of less than 30 minutes;

operating conditions permitting elimination of the risk of auto-oxidation of the thiol groups during the assay period.

DETAILED DESCRIPTION OF THE INVENTION

These aims are achieved by virtue of the invention which, according to one of these embodiments, provides a process for assaying mercaptans in an aqueous sample, especially a biological sample, characterized in that it essentially comprises the formation of a chromophoric substitution product between all the mercaptans present in the sample and a reagent chosen from the quinolinium type compounds corresponding to general formula I: in which:

$$\begin{array}{c} R^4 \quad R^3 \\ R^5 \\ R^6 \\ R^7 \quad R^1 \end{array} \quad R^2, Y^- \quad (I)$$

in which:
$R^1$=alkyl (with 1 to 6 carbon atoms), benzyl, p-nitrobenzyl, phenyl or o,p-dinitrophenyl;
$R^2$=hydrogen or methyl;
$R^3$=hydrogen, F, Cl, Br, I or SCN;
$R^4$=hydrogen, F, Cl, $NO_2$ or $CF_3$;
$R^5$=hydrogen, $NO_2$ or Cl;
$R^6$=hydrogen, F, Cl, $CF_3$ or $NO_2$;
$R^7$=hydrogen, OH, benzyloxy or $NO_2$;
it being understood that $R^3$, $R^4$, $R^5$ and $R^6$ cannot simultaneously represent hydrogen, and
Y=fluoride, chloride, bromide, iodide, methyl sulphate, fluorosulphonate, phosphate, tetrafluoroborate or tosylate.

The compounds of general formula I above can be prepared, from commercial compounds, by analogy with known processes and especially as follows.

The derivatives of the fluoroquinolinium series are obtained by Schiemann reaction on the corresponding diazonium salts, themselves prepared from commercial compounds.

A general procedure for the last step of synthesis of the compounds of general formula I is carried out as follows.

To the quinoline derivative (1 mmol) dissolved in 10 volumes of an organic solvent, such as for example acetonitrile, is added at 10° C. the alkylating agent either pure, such as for example methyl iodide, or in solution in an organic solvent, such as for example trimethyloxonium tetrafluoroborate (2 mmol) in 1 volume of acetonitrile. The reaction medium is stirred for 30 minutes to 2 hours. The solvent in evaporated under reduced pressure, the residue is taken up in 1 volume of tert-butyl methyl ether, then drained, washed and dried under vacuum.

When necessary, the products are purified by preparative high-performance liquid chromatography (HPLC) on a silica column (C8, 5 µm), eluting with a water/acetonitrile mixture. A final freeze-dry makes it possible to obtain the desired products with non-optimized yields of between 20 and 89%.

When appropriate, the alkylation is carried out in methyl iodide under reflux, or by means of methyl sulphate in acetone under reflux or methyl fluorosulphonate in organic solvent, such as for example glyme, according to the final product desired.

The compounds of general formula I in which:
$R^1$, $R^3$, $R^6$ and $R^7$ are defined as above;
$R^2$=hydrogen;

$R^4$=hydrogen, F, Cl or $CF_3$;
$R^5$=hydrogen or Cl; and
Y=fluoride, chloride, bromide, methyl sulphate, fluorosulphonate, phosphate, tetrafluoroborate or tosylate, it being understood that:
  when $R^3$=F, Cl, Br or I, then $R^2$, $R^4$, $R^5$, $R^6$ and $R^7$ cannot simultaneously represent H;
  when $R^4$=F or Cl, then $R^2$, $R^3$, $R^5$, $R^6$ and $R^7$ cannot simultaneously represent H;
  when $R^5$=Cl, then $R^2$, $R^3$, $R^4$, $R^6$ and $R^7$ cannot simultaneously represent H;
  when $R^6$=F or Cl, then $R^2$, $R^3$, $R^4$, $R^5$ and $R^7$ cannot simultaneously represent H;
  when $R^3$=$R^6$=Cl, then $R^2$, $R^4$, $R^5$ and $R^7$ cannot simultaneously represent H; and
  when $R^6$=Cl or $R^7$=OH, then Y cannot represent methyl sulphate, are new and constitute one of the subjects of the present invention.

According to another embodiment, the invention provides a process for assaying reduced glutathione (GSH) in an aqueous sample, especially a biological sample, characterized in that it essentially comprises the steps consisting of:
1. forming a chromophoric substitution product between all the mercaptans present in the sample and a reagent chosen from the compounds of general formula I defined above; and
2. bringing the pH of the reaction medium to a value between 12.8 and 13.8, in order to form specifically a chromophoric thione from the chromophoric substitution product formed in step 1. between GSH and the said reagent.

The principle of the reduced glutathione assay according to the invention is therefore based on a strategy comprising two consecutive chemical steps:
first of all, formation of a substitution product, hereinbelow called "adduct", between all the mercaptans (RSH) present in the sample, especially including reduced glutathione (GSH), and one of the reagents defined above, called "BXT reagent", according to the reaction:

RSH+BXT reagent→RS-BXT (chromophore 1)

then, after alkalization of the medium, to a pH of between 12.8 and 13.8, according to the BXT reagent used, formation, by β-elimination reaction, of a chromophoric thione, specific for the adduct GS-BXT, formed from GSH and the BXT reagent, according to the reaction:

GS—BXT $\xrightarrow{\text{pH alkaline}}$ thione (chromophore 2).

This method makes it possible to determine, by means of spectrophotometric measures:
in a first instance, the quantity of total mercaptans (RSH) present in the sample;
in a second instance, the quantity of reduced glutathione (GSH) in the same sample; and
by subtraction, the quantity of mercaptans distinct from reduced glutathione.

This method therefore makes it possible to have access to three parameters by means of a single sample.

The novelty of the assay process according to the invention is based on a strategy comprising a first step of formation of a chromophoric adduct between the BXT reagent and all the mercaptans present in the sample and a second step, after alkalization, of formation of a chromophoric thione, specifically with the adduct GSH/BXT reagent.

The use of the reagents and of the process which are described therefore makes it possible to measure, on a single sample, the overall quantity of mercaptans, in general, and that of GSH, in particular, in aqueous medium by means of a double calorimetric measurement. The simplicity of implementation of this novel method is very superior to that of the spectrophotometric methods previously described. The method for the colorimetric assay of GSH which is described here is the first to be totally specific in the absence of any enzymatic reagent.

This new assay method therefore constitutes a novel tool for biological research in general and for Clinical Chemistry, in particular for the production of assay or diagnostic kits, the potential physiopathologies being for example cataract, diabetes, rheumatoid arthritis, ischemia.

The samples of interest are especially erythrocytes, plasma, blood platelets, and in general any sample, especially a biological sample, containing mercaptans and in particular GSH.

According to an advantageous embodiment, the subject of the invention is a process for assaying total mercaptans in an aqueous sample, especially a biological sample, characterized in that it comprises essentially the steps consisting of:
1. adding to the sample to be assayed, buffered within the pH range of 7.0 to 7.5, an aliquot of a stock solution, in water or a water-miscible solvent, of a BXT reagent of general formula I in excess,
2. homogenizing the reaction medium thus obtained,
3. leaving to incubate for at least 5 minutes,
4. measuring, by means of a spectrophotometer, the absorbance of the substitution product(s) or adduct(s) formed between the BXT reagent and the mercaptan(s) present in the sample and
5. determining the concentration, in moles/liter of total mercaptans present in the sample, according to the formula:

[total mercaptans]=(A/ϵm×d)×D in which:
A represents the absorbance measured,
ϵm represents the specific molar extinction coefficient for the BXT reagent used, expressed in $1.\text{mole}^{-1}.\text{cm}^{-1}$,
d represents the cuvette length, expressed in cm, and
D represents the coefficient of dilution.

According to another advantageous embodiment, the subject of the invention is a process for assaying reduced glutathione, GSH, in an aqueous sample, especially a biological sample, characterized in that it comprises essentially the steps consisting of:
1. adding to the sample to be assayed, buffered within the pH range of 7.0 to 7.5, an aliquot of a stock solution, in water or in a water-miscible solvent, of a BXT reagent of general formula I in excess,
2. homogenizing the reaction medium thus obtained,
3. leaving to incubate for at least 5 minutes,
4. adjusting the pH of the mixture to a value of between 12.8 and 13.8, according to the BXT reagent chosen,
5. leaving to incubate for at least 15 minutes,
6. measuring, by means of a spectrophotometer, the absorbance of the chromophoric thione produced by β-elimination, specifically with the adduct GSH-BXT reagent and
7. determining the concentration in moles/litre of GSH in the sample, according to the formula:

[GSH]=(A'/ϵm×d)×D in which:

A' represents the absorbance measured,

εm represents the specific coefficient of molar extinction of the BXT reagent used, expressed in $1.\text{mole}^{-1}.\text{cm}^{-1}$, d represents the cuvette length, expressed in cm, and D represents the coefficient of dilution.

According to still another advantageous embodiment of the invention, the concentration of mercaptans distinct from reduced glutathione which are present in the sample, is measured by subtraction of the concentrations measured according to the two processes defined above, that is to say by using the formula:

[mercaptans distinct from GSH]=[total mercaptans]−[GSH].

The assay of total mercaptans, of reduced glutathione and of mercaptans other than GSH in an aqueous sample, especially a biological sample, by means of the new reagents of general formula I, is therefore based on the spectrophotometric measurement of the formation of the new chromophores 1 and 2, which are respectively produced during each of the two reactions constituting this novel method.

General methods which can be used for carrying out these determinations are explained in greater detail below.

Assay of total mercaptans:

The reaction medium consists of a buffer of pH=7.0 to 7.5, such as, for example, a 50 mM phosphate buffer, containing a 1 mM diethylenetriaminepentacetic acid (DTPA). According to the nature of the buffer considered, an addition of sodium hydroxide or hydrochloric acid, at room temperature, makes it possible to adjust the pH to the desired value. The working temperature chosen, for example 25° C., should be maintained constant (±3° C.) during the incubation and measurement periods. The buffer and reagent solutions should be prepared and preserved between 0° and 4° C. Under these conditions, these solutions are stable for 3 months. The ratio concentration of BXT reagent/estimated concentration of mercaptans should be greater than or equal to 10 and generally does not exceed 1000, in order to ensure short reaction times.

The reaction is started by the addition, for example into a spectrophotometer cuvette containing the samples to be assayed, of an aliquot of a stock solution of BXT reagent in water or in a water-miscible organic solvent, such as for example ethanol, acetonitrile, dimethylformamide or dimethylsulphoxide. The final reaction volume, for example 1 ml, should not vary from one measurement to another.

After homogenization of the solution and incubation for 5 to 10 minutes at the working temperature chosen, the absorbance at the wavelength of the adduct or adducts is measured: for example at 356 nm for the adduct between the compound BXT03015 according to the invention, which is described in Example 1 of the experimental part below, and GSH.

Table I below contains, by way of examples, the spectrophotometric data obtained with the reagent XT03015 and a number of physiological mercaptans or which are capable of being used in biochemistry or Clinical Chemistry.

TABLE I

Spectral data for the chromophores obtained by reaction between reagent BXT03015 and some mercaptans, before and after alkalization

| Mercaptans | BEFORE alkalization | AFTER alkalization |
|---|---|---|
| | Adduct of BXT03015 λmax (nm), εm $(1 \cdot \text{mole}^{-1} \cdot \text{cm}^{-1})$ | λmax (nm), εm $(1 \cdot \text{mole}^{-1} \cdot \text{cm}^{-1})$ |
| Glutathione | 356,16000 | thione: 400,14700 |
| DL-Penicillamine | 354,16000 | adduct: 358,15000 |
| N-acetyl-L-cysteine | 358,15000 | hydrolyse: 329,10500 |
| Mercaptosuccinate | 362,15000 | hydrolyse: 329,10800 |
| Cysteine | 352,18500 | adduct: 356,18400 |
| Homocysteine | 352,15000 | adduct: 356,14000 |
| 2-mercaptopyridine | 345,14500 | hydrolyse: 327,13000 |
| Diethyldithio-carbamate | 279,13000 | hydrolyse: 329,10400 |
| Captopril | 359,14000 | hydrolyse: 329,10300 |
| Thio-β-D-glucose | 341,14000 | hydrolyse: 329,10700 |
| Cysteinylglycine | 350,16000 | adduct: 355,13000 |
| Coenzyme A | 359,16000 | hydrolyse: 329,8000 |
| Bovine serum albumine | (*) 345,12500 | (**) |

(*) Only 0.50 equivalent of adduct is formed (see reference 21).
(**) The absorption spectrum is similiar to that obtained before alkalization.

The quantification of the total mercaptans is performed as indicated above.

The sensitivity of the assay was determined from a calibration series for certain physiologically important mercaptans. It is, for example for GSH, equal to 0.017 $\text{AU}.1.\mu\text{mol}^{-1}$ with the reagent BXT03015, as is evident from the examination of FIG. 1 of the accompanying drawings (AU=absorbance units).

Figure 1:
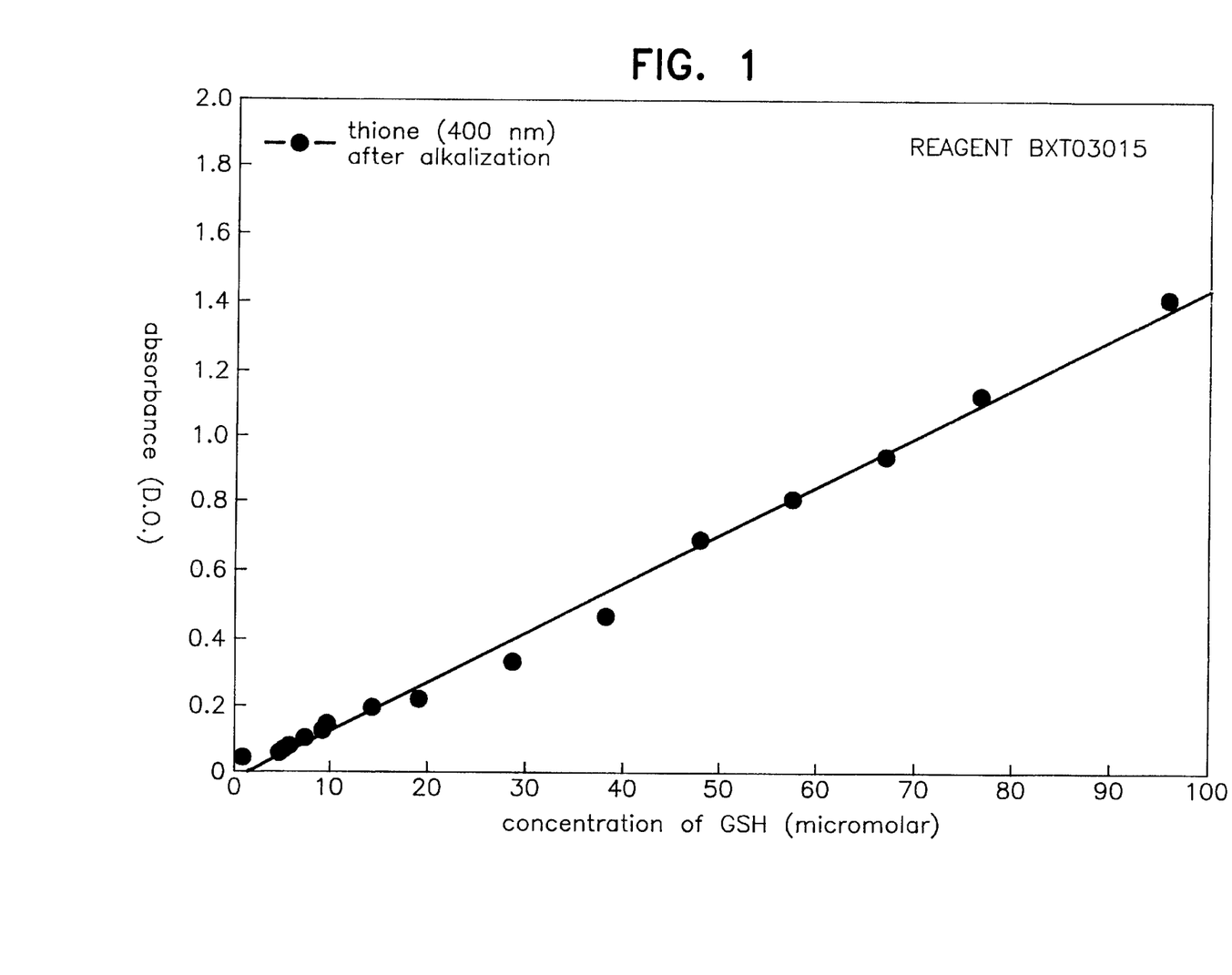
FIGS. 1–3 show concentration dependent variation of absorbance for the adducts of several compounds with the BXT3015 reagent.

FIG. 1 represents the variations of the absorbance at 356 nm of the adduct formed between the reagent BXT03015 and GSH, N-acetylcysteine, cysteine and cysteinylglycine, respectively, as a function of the micromolar concentration of mercaptans.

It can be observed that the absorbance varies linearly as a function of this concentration and that the sensitivity of the assay is equal to 0.017 $\text{AU}.1.\mu\text{mol}^{-1}$, for GSH.

Assay of reduced glutathione:

The same reaction mixture, used above for the assay of the total mercaptans, is re-used for the assay of reduced glutathione. This mixture is adjusted to a pH value=13.5 by the addition of a concentrated alkaline solution, such as for example a 0.30 % solution of sodium hydroxide, at the working temperature chosen, for example 25° C. After 15–20 minutes of incubation under these same conditions, the absorbance of the single product of β-elimination of the adduct between GSH and the BXT reagent, is measured at the wavelength defined for the BXT reagent considered, for example 400 nm for the reagent BXT03015. Table II below contains the spectrophotometric data obtained with some reagents according to the invention and GSH.

TABLE II

Spectral data for the chromophores obtained by reaction between GSH and some BXT reagents whose preparation is described in the experimental part below, before and after alkalisation

| | | BEFORE | AFTER |
|---|---|---|---|
| | | alkalization | |
| No. | BXT REAGENT $\lambda$max (nm) $\epsilon$m $(1 \cdot mol^{-1} \cdot cm^{-1})$ | Adduct $\lambda$max (nm) $\epsilon$m $(1 \cdot mol^{-1} \cdot cm^{-1})$ | Thione $\lambda$max (nm) $\epsilon$m $(1 \cdot mol^{-1} \cdot cm^{-1})$ |
| BXT 03015 (Ex. 1) | 315 8000 | 356 16000 | 400 14700 |
| BXT 03016 (Ex. 2) | 321 12000 | 339 15000 | 381 16000 |
| BXT 03034 (Ex. 3) | 319 9000 | 346 15000 | 388 18000 |
| BXT 03065 (Ex. 5) | 326 9000 | 343 17000 | 393 20000 |
| BXT 03069 (Ex. 9) | 312 5400 | 414 6000 | 520 2500 |

Figure 3:
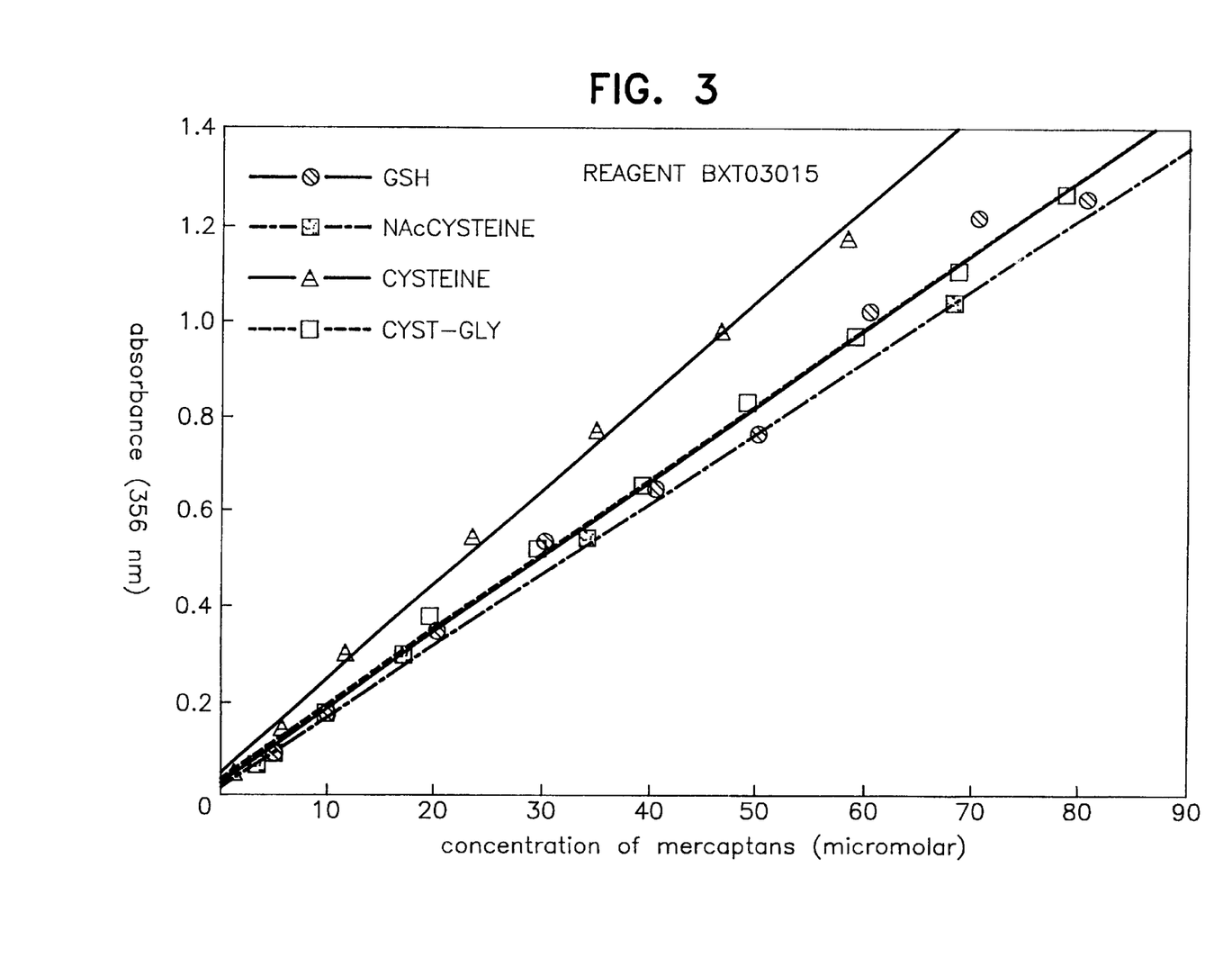

The sensitivity of the assay is determined from a standard range of GSH concentrations, and is for example equal to 0.010 AU.1.$\mu$mol$^{-1}$ with the reagent BXT03015, as shown by FIG. 3 of the accompanying drawings.

Figure 2:
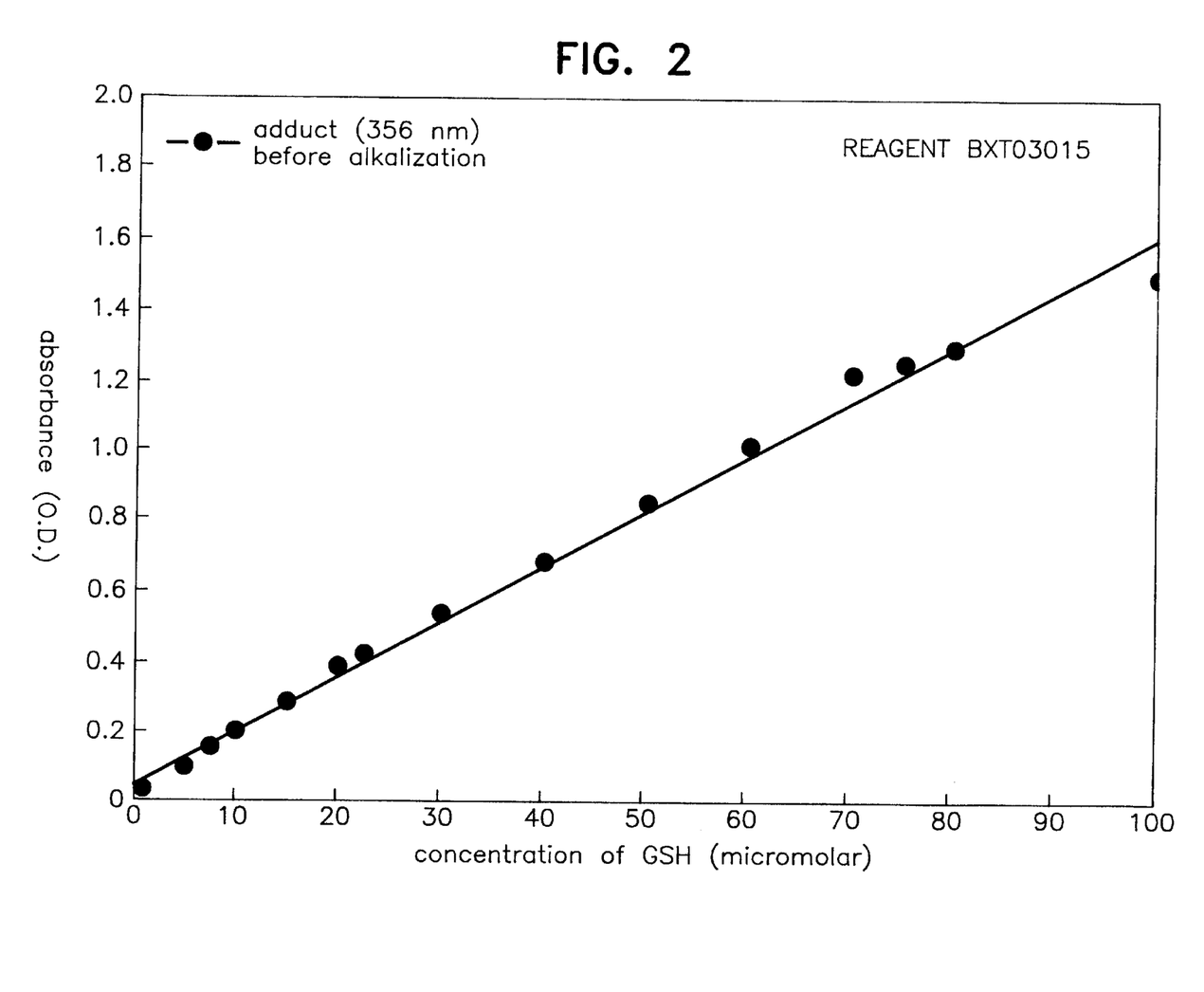

FIG. 2 represents the variations of the absorbance or optical density (O.D.) at 356 m of the adduct formed between GSH and the reagent BXT03015, before alkalization, as a function of the (micromolar) concentration of GSH.

It can be observed that the absorbance varies linearly as a function of the GSH concentration. This figure shows, in addition, the sensitivity of the assay.

FIG. 3 represents the variations of the absorbance or optical density (O.D.) at 400 nm of the thione formed from the adduct GSH/BXT03015 reagent, after alkalization, as a function of the (micromolar) concentration of GSH.

It can be observed that the absorbance varies linearly as a function of the concentration of GSH. This figure shows, in addition, the sensitivity of the assay.

The subject of the invention is, in addition, a set or kit for implementing the processes according to the invention which are defined above, characterized in that it comprises essentially, as reagent, a compound of general formula I.

The invention will be explained in greater detail by means of the non-limitative examples given in the experimental part below.

EXPERIMENTAL PART

I. EXAMPLES OF SYNTHESIS OF REAGENTS OF GENERAL FORMULA I

Example 1

4-chloro-7-trifluoromethyl-1-methylguinolinium tetrafluoroborate (BXT03015).

2.15 mmol of 4-chloro-7-trifluoromethylquinoline (ALDRICH) are dissolved, with stirring, in 5 ml of acetonitrile, in a 50 ml round-bottomed flask provided with stirring, a thermometer and under a nitrogen stream. At 10° C. a solution of 4.30 mmol of trimethyloxonium tetrafluoroborate (LANCASTER) in 4 ml of acetonitrile is added over 10 minutes. The stirring is maintained for 1 hour and the solvent is evaporated under vacuum. The crude residue is taken up in 50 ml of tert-butyl methyl ether, drained and dried under vacuum for 2 hours.

The crude product is purified by preparative HPLC on a column ($C_8$, 5 $\mu$m, L=250 mm, ID=10.5 mm), eluting with an acetonitrile-water mixture (20/80). After freeze-drying, the desired product (1.7 mmol) is obtained.

Yield 77%. Physical characteristics: *$^1$H NMR (200 MHz, $CD_3COCD_3$): $CH_3$—$N^+$: 5.00 ppm (s, 3H); $H_6$: 8.45 ppm (dd, 1H, J=1.9–9.5 Hz); $H_3$: 8.60 ppm (d, 1H, J=7.14 Hz); $H_5$: 8.95 ppm (d, 1H, J=9.50 Hz); $H_8$: 9.10 ppm (s, 1H); $H_2$: 9.70 ppm (d, 1H, J=7.14 Hz). *MS: (FAB, glycerol-NOBA) positive ion: $M^+$: 246 negative ion: $M^-$: 87.

FAB=Fast Atom Bombardment
NOBA=meta-nitrobenzyl alcohol
*Microanalysis:
Calculated (%): C=39.6; H=2.4; N=4.2; Cl=10.6 Found (%): C=39.4; H=2.2; N=4.0; Cl=10.2.

Example 2

4-chloro-1,2-dimethylguinolinium tetrafluoroborate (BXT03016).

2.0 mmol of 4-chloro-2-methylquinoline (ALDRICH) are dissolved, with stirring, in 5 ml of acetonitrile, in a 50 ml round-bottomed flask provided with stirring, a thermometer and under a nitrogen stream. At 10° C. a solution of 4.0 mmol of trimethyloxonium tetrafluoroborate (LANCASTER) in 4 ml of acetonitrile is added over 10 minutes. The stirring is maintained for 1 hour and the solvent is evaporated under vacuum. The crude residue is taken up in 50 ml of tert-butyl methyl ether, drained and dried under vacuum for 2 hours.

The crude product is purified by preparative HPLC on a column ($C_8$, 5 $\mu$m, L=250 mm, ID=10.5 mm), eluting with an acetonitrile-water mixture (20/80). After freeze-drying, the desired product (0.8 mmol) is obtained.

Yield 38%. Physical characteristics: *$^1$H NMR (200 MHz, $CD_3COCD_3$) $CH_3$: 3.2 ppm (s, 3H); $CH_3$-$N^+$: 4.70 ppm (s, 3H); $H_7$: 8.10 ppm (dd, 1H, J=8–6.5 Hz); $H_6$: 8.30 ppm (dd, 1H, J=8–6.5 Hz); $H_3$: 8.40 ppm (s, 1H); $H_5$: 8.60 ppm (d, 1H, J=8 Hz); $H_8$: 8.70 ppm (d, 1H, J=8 Hz). *MS: (FAB, glycerol-NOBA) positive ion: $M^+$: 192 negative ion: $M^-$: 87 *Microanalysis: Calculated (%): C=47.2; H=3.9; N=5.0; Cl=12.7; Found (%): C=47.3; H=3.9; N=4.9; Cl=13.0.

Example 3

4-chloro-1-methylquinolinium tetrafluoroborate (BXT03034).

3.17 mmol of 4-chloroquinoline (ALDRICH) are dissolved, with stirring, in 10 ml of acetonitrile, in a 100 ml round-bottomed flask provided with stirring, a thermometer and under a nitrogen stream. At room temperature a solution of 6.30 mmol of trimethyloxonium tetrafluoroborate (LANCASTER) in 4 ml of acetonitrile is added over 10 minutes. The stirring is maintained for 30 minutes and the solvent is evaporated under vacuum. The crude residue is taken up in 10 ml of 2-propanol and stirred for 10 minutes. The precipitate is filtered, washed with 50 ml of tert-butyl methyl ether, drained and dried under vacuum for 2 hours.

After recrystallization from a tert-butyl methyl ether/2-propanol mixture (1/1), the desired product (1.5 mmol) is obtained.

Yield: 84%. Physical characteristics: *$^1$H NMR (200 MHz, $CD_3COCD_3$) $CH_3$-N+: 4.45 ppm (s, 3H); $H_3$: 8.20 ppm (d, 1H, J=7.5 Hz); $H_6$ and $H_7$: 8.40 ppm (m, 2H); $H_5$ and $H_8$: 8.70 ppm (dd, 2H, J=8–1.8 Hz); $H_2$: 9.5 ppm (d, 1H, J=7.5 Hz). *MS: (FAB, glycerol-NOBA) positive ion: M$^+$: 178 negative ion: M$^-$: 87.

Example 4

7-chloro-1,2-dimethylquinolinium tetrafluoroborate (BXT03064).

2.0 mmol of 7-chloro-2-methylquinoline (ALDRICH) are dissolved, with stirring, in 5 ml of acetonitrile, in a 50 ml round-bottomed flask provided with stirring, a thermometer and under a nitrogen stream. At 10° C. a solution of 2.60 mmol of trimethyloxonium tetrafluoroborate (LANCASTER) in 4 ml of acetonitrile is added over 10 minutes. The stirring is maintained for 1 hour 30 minutes and the solvent is evaporated under vacuum. A crude residue is taken up in 50 ml of tert-butyl methyl ether, drained and dried under vacuum for 2 hours.

After recrystallization from a tert-butyl methyl ether/2-propanol mixture (1/1), the desired product (1.5 mmol) is obtained.

Yield: 76%. Physical characteristics: *$^1$H NMR (200 MHz, $CD_3COCD_3$) $CH_3$: 3.20 ppm (s, 3H); $CH_3$—N$^+$: 4.65 ppm (s, 3H); $H_6$: 8.00 ppm (dd, 1H, J=8.8–1.6 Hz); $H_3$: 8.12 ppm (d, 1H, J=8 Hz); $H_5$: 8.45 ppm (d, 1H, J=8.8 Hz); $H_8$: 8.7 2 ppm (d, 1H, J–1.8 Hz); $H_4$: 9.12 ppm (d, 1H, J=8 Hz). *MS: (FAB, glycerol-NOBA) positive ion: M$^+$: 192 negative ion: M$^-$: 87. *Microanalysis: Calculated (%) : C=47.2; H=3.9; N=5.0; Cl=12.7 Found (%): C=47.0; E=3.8; N=5.1; Cl=12.5.

Example 5

4.7-dichloro-1-methylquinolinium tetrafluoroborate (BXT03065).

2.0 mmol of 4,7-dichloroquinoline (ALDRICH) are dissolved, with stirring, in 5 ml of acetonitrile, in a 50 ml round-bottomed flask provided with stirring, a thermometer and under a nitrogen stream. At 10° C. a solution of 2.60 mmol of trimethyloxonium tetrafluoroborate (LANCASTER) in 4 ml of acetonitrile is added over 10 minutes. The stirring is maintained for 1 hour and the solvent is evaporated under vacuum. The crude residue is taken up in 50 ml of tert-butyl methyl ether, drained and dried under vacuum for 2 hours.

After recrystallization from a tert-butyl methyl ether/2-propanol mixture (1/1), the desired product (1.4 mmol) is obtained.

Yield: 70%. Physical characteristics: *$^1$H NMR (200 MHz, $D_2O$): $CH_3$—N$^+$: 7 ppm (s, 3H); $H_6$: 10.49 ppm (dd, 1H, J=9–2.2 Hz); $H_3$: 10.58 ppm (d, 1H, J=6.7 Hz); $H_8$: 10.94 ppm (d, 1H, J=2.1 Hz); $H_5$: 11.2 ppm (d, 1H, J=9 Hz); $H_2$: 11.56 ppm (d, 1H, J=6.5 Hz). *MS: (FAB, glycerol-NOBA) positive ion: M$^+$: 212 negative ion: M$^-$: 87. *Microanalysis: Calculated (%): C=40.0; H=2.6; N=4.6; Cl=23.6 Found (%): C=41.1; H=2.4; N=4.8; Cl=23.6.

Example 6

5-chloro-8-hydroxy-1-methylquinolinium tetrafluoroborate (BXT03066).

2.0 mmol of 5-chloro-8-hydroxyquinoline (ALDRICH) are dissolved, with stirring, in 5 ml of acetonitrile, in a 50 ml round-bottomed flask provided with stirring, a thermometer and under a nitrogen stream. At 10° C. a solution of 2.40 mmol of trimethyloxonium tetrafluoroborate (LANCASTER) in 4 ml of acetonitrile is added over 10 minutes. The stirring is maintained for 30 minutes and the solvent is evaporated under vacuum. A crude residue is taken up in 50 ml of tert-butyl methyl ether, drained and dried under vacuum for 2 hours.

After recrystallization from a tert-butyl methyl ether/2-propanol mixture (1/1), the desired product (1.4 mmol) is obtained.

Yield: 70 %. Physical characteristics: *$^1$H NMR (200 MHz, $CD_3COCD_3$) $CH_3$—N$^+$: 5.05 ppm (s, 3H); $H_7$: 7.65 ppm (d, 1H, J=8.6 Hz); $H_6$: 7.95 ppm (d, 1H, J=8.6 Hz); $H_3$: 8.20 ppm (dd, 1H, J=5.7–2.3 Hz); $H_4$: 9.35 ppm (d, 1H, J=5.7 Hz); $H_2$: 9.40 ppm (d, 1H, J=2.3 Hz). *MS: (FAB, glycerol-NOBA) positive ion: M$^+$: 194 negative ion: M$^-$: 87.

Example 7

5-chloro-8-benzyloxy-1-methylquinolinium tetrafluoroborate (BXT03063).

5-Chloro-8-benzyloxyquinoline:

10.0 mmol of 5-chloro-8-hydroxyquinoline (ALDRICH) are dissolved, with stirring, in 20 ml of dry DMF, in a 50 ml round-bottomed flask provided with stirring and a thermometer. Then 11 mmol of potassium carbonate and 10% by weight of potassium iodide are added. A solution of 11 mmol of benzyl chloride (JANSSEN) in 5 ml of DMF is added dropwise over 5 minutes, at room temperature and with stirring. After 18 hours of reaction at 50° C., the reaction mixture, supplemented with 100 ml of water is extracted with 4×50 ml of tert-butyl methyl ether. The organic phases are combined, then washed with 3×50 ml of 1N HCl. The aqueous phases are combined, alkalized to pH=9 and extracted with 2×50 ml of ethyl acetate. After drying the organic phase over $MgSO_4$, the solvent is evaporated under reduced pressure. The desired product is obtained after recrystallization from ethanol.

Yield: 79.5%. Physical characteristics: *$^1$H NMR (200 MHz, $CD_3COCD_3$) $CH_{2O}$: 5.35 ppm (s, 2H); 7.22–7.45 ppm (m, 4H); 7.55–7.70 ppm (m, 4H); $H_4$: 8.53 ppm (d, 1H, J=5.2 Hz); $H_2$: 8.95 ppm (d, 1H, J=2.1 Hz).

5-Chloro-8-benzyloxy-1-methylquinolinium tetrafluoroborate (BXT03063) :

10.0 mmol of 5-chloro-8-benzyloxyquinoline are dissolved, with stirring, in 5 ml of acetonitrile, in a 50 ml round-bottomed flask provided with stirring, a thermometer and under a nitrogen stream. At 10° C. a solution of 23.0 mmol of trimethyloxonium tetrafluoroborate (LANCASTER) in 4 ml of acetonitrile is added over 10 minutes. The stirring is maintained for 1 hour and the solvent is evaporated under vacuum. The crude residue is taken up in 50 ml of tert-butyl methyl ether, drained and dried under vacuum for 2 hours.

The crude product is purified by preparative HPLC on a column ($C_8$, 5 µm, L=250 mm, ID=10.5 mm), eluting with an acetonitrile-water mixture (20/80). After freeze-drying, the desired product (2 mmol) is obtained.

Yield: 21%. Physical characteristics: *$^1$H NMR (200 MHz, $CD_3COCD_3$) $CH_3$—N$^+$: 5.00 ppm (s, 3H); $CH_{2O}$:

5.55 ppm (s, 2H); $H_2$, $H_4$, and $H_6$,: 7.45 ppm (m, 3H); $H_3$, and $H_5$,: 7.75 ppm (m, 2H); $H_7$: 7.95 ppm (d, 1H, J=10 Hz); $H_6$: 8.15 ppm (d, 1H, J=10 Hz), $H_3$: 8.35 ppm (t, 1H, J=11.2 Hz); $H_2$ and $H_4$: 9.5 ppm (d, 2H, J=11.4 Hz). *MS: (FAB, glycerol-NOBA) positive ion: $M^+$: 284 negative ion: $M^-$: 87.

Example 8

5-fluoro-1-methylquinolinium tetrafluoroborate (BXT03068).

5-fluoroquinoline:

13.7 mmol of 5-aminoquinoline (ALDRICH) are dissolved, at room temperature, in 20 ml of ethanol in a 100 ml three-necked round-bottomed flask provided with stirring and a thermometer. A 34% tetrafluoroboric acid solution is added over 5 minutes. The reaction mixture is cooled to –5° C. and 36.0 mmol of isoamyl nitrite (JANSSEN) are added over 10 minutes at this temperature. At the end of the addition, the reaction medium is maintained at 0° C., with stirring, for 1 hour. The suspension obtained is filtered, the solid is washed with 3×20 ml of absolute ethanol and 3×20 ml of ethyl ether, then dried under vacuum for 18 hours. The diazonium salt thus obtained with a yield of 85.7% is used as it is for the next step.

The diazonium salt obtained above is suspended in 100 ml of anhydrous heptane and heated under reflux for 3 hours, with stirring, in a 250 ml three-necked round-bottomed flask provided with stirring, a thermometer and a return condenser, which is itself equipped with an oil bubbler. The reaction mixture is cooled and supplemented with a 1N sodium hydroxide solution (100 ml). The organic phase is decanted, washed with 2×100 ml of this same sodium hydroxide solution, then with 2×100 ml of NaCl-saturated water and dried over $MgSO_4$. The solvent is evaporated under vacuum with a rotary evaporator.

The desired product is purified by column chromatography on Geduran® silica [MERCK, 40–63 μm (230–400 mesh)]: eluent $CH_2Cl_2$.

Yield: 35%. Physical characteristics: *¹H NMR (200 MHz, $CDCL_3$): $H_6$: 7.26–7.40 ppm (ddd, 1H, J=1–6.8–9.7 Hz); $H_3$: 7.54–7.64 ppm (dd, 1H, J=4.8–10 Hz); $H_7$: 7.67–7.79 ppm (ddd, 1H, J=4–6.8–8 Hz); $H_8$: 7.88 ppm (dd, 1H, J=1–8 Hz); $H_4$: 8.45 ppm (dd, 1H, J=2–10 Hz); $H_2$: 8.95 ppm (dd, 1H, J=2–4.8 Hz). *MS: (EI, 70eV) $M^+$: 147(100); 120(21); 99(10); 74(14). EI=electron impact 5-Fluoro-1-methylquinolinium tetrafluoroborate (BXT03068):

10.0 mmol of 5-fluoroquinoline are dissolved, with stirring, in 5 ml of acetonitrile, in a 50 ml round-bottomed flask provided with stirring, a thermometer and under a nitrogen stream. At 10° C. a solution of 23.0 mmol of trimethyloxonium tetrafluoroborate (LANCASTER) in 4 ml of acetonitrile is added over 10 minutes. The stirring is maintained for 1 hour and the solvent is evaporated under vacuum. The crude residue is taken up in 50 ml of tert-butyl methyl ether, drained and dried under vacuum for 2 hours.

The desired product is recrystallized from a tert-butyl methyl ether/2-propanol mixture (1/1).

Yield: 50%. Physical characteristics: *¹H NMR (200 MHz, $CD_3COCD_3$): $CH_3$—$N^+$: 4.90 ppm (s, 3H); $H_3$: 7.85 ppm (dd, 1H, J=9.5–12 Hz); $H_6$ and $H_7$: 8.25–8.40 ppm (m, 2H); $H_8$: 8.48 ppm (d, 1H, J=12.3 Hz); $H_4$: 9.45 ppm (d, 1H, J=12 Hz); $H_2$: 9.65 ppm (d, 1H, J=9.5 Hz). *MS: (EI, 70eV) $M^+$: 162(80); 147(100); 120(48); 99(21); 74(20).

Example 9

5-fluoro-8-nitro-1-methylquolinium fluorosulphonate (BXT03069).

5-Fluoro-8-nitroquinoline:

A solution of 20.0 mmol of 5-fluoroquinoline is introduced into 10 ml of concentrated sulphuric acid (d=1.84), in a 100 ml three-necked round-bottomed flask, provided with stirring and a thermometer. While the temperature is maintained at 0° C., 5 ml of fuming nitric acid are added dropwise, with stirring. The reaction mixture is maintained at 20° C. for 10 minutes, then slowly poured over ice (100 g). The reaction mixture is brought to pH=8 by slow addition of concentrated sodium hydroxide. The precipitate thus obtained is extracted with 100 ml of ethyl acetate. The organic phase is washed with 2×50 ml of water and dried over $MgSO_4$. The solvent is evaporated under reduced pressure.

The desired product is purified by column chromatography on Geduran(s silica: eluent $CH_2Cl_2$.

Yield : 67%. Physical characteristics: *¹H NMR (200 MHz, $CDCl_3$): $H_6$: 7.27 ppm (dd, 1H, J=8.58–8.64 Hz); $H_3$: 7.62 ppm (dd, 1H, J=8.60–4.20 Hz); $H_7$: 8.10 ppm (dd, 1H, J=8.56–5.22 Hz), $H_4$: 8.48 ppm (dd, 1H, J=2.5–8.6 Hz); $H_2$: 9.12 ppm (dd, 1H, J=2.5–4.2 Hz). *MS: (EI, 70eV) $M^+$: 192(100), 176(16), 162(47), 146(33), 134(98), 126(43), 119 (21), 107(36), 99(44). 5-Fluoro-8-nitro-1-methylquinolinium fluorosulphonate (BXT03069):

2.5 mmol of 5-fluoro-8-nitroquinoline are dissolved, with stirring, in 10 ml of dry glyme, in a 100 ml three-necked round-bottomed flask provided with stirring, a thermometer, and under a nitrogen stream. At room temperature, 1 ml of methyl fluorosulphonate (10 mmol; ALFA VENTRON) is added over 3 minutes. The reaction mixture is stirred for 1 hour at 60° C. After returning to room temperature, the precipitate obtained is drained and washed with 3×10 ml of tert-butyl methyl ether and then dried under vacuum. The desired product is obtained with a yield of 46%. Physical characteristics: *¹H NMR (200 MHz, $CD_3COCD_3$): $CH_3$—$N^+$: 4.70 ppm (s, 3H); $H_6$: 8.10 ppm (dd, 1H, J=8.46–8.56 Hz); $H_3$: 8.58 ppm (dd, 1H, J=8.72–5.86 Hz); $H_7$: 8.90 ppm (dd, 1H, J=8.72–5.28 Hz); $H_4$: 9.66 ppm (d, 1H, J=8.8 Hz); $H_2$: 9.88 ppm (d, 1H, J=5.86 Hz). *MS: (FAB, glycerol-NOBA) positive ion: $M^+$: 207 negative ion: $M^-$: 404 (2 $M^-$/1 $M^+$) $M^-$: 99.

Example 10

5-nitro-1-methylquinolinium tetrafluoroborate (BXT03070).

5.74 mmol of 5-nitroquinoline (ALDRICH) are dissolved, with stirring, in 10 ml of acetonitrile, in a 50 ml round-bottomed flask provided with stirring, a thermometer and under a nitrogen stream. At 25° C. a solution of 6.4 mmol of trimethyloxonium tetrafluoroborate (LANCASTER) in 4 ml of acetonitrile is added over 10 minutes. The stirring is maintained for ½ hour and the solvent is evaporated under vacuum. The crude residue is taken up in a tert-butyl methyl ether/2-propanol mixture (1/1), drained and dried under vacuum for 2 hours.

The desired product is recrystallized from a tert-butyl methyl ether/2-propanol mixture (1/1).

Yield: 89%. Physical characteristics *¹H NMR (200 MHz, $D_2O$): $CH_3$—$N^+$: 4.70 ppm (s, 3H); $H_3$: 8.20 ppm (dd, 1H, J=9.6–5.6 Hz); $H_7$: 8.33 ppm (t, 1H, J=8.6 Hz); $H_6$ and $H_8$: 8.74 ppm (t, 2H, J=8.6 Hz); $H_4$: 9.37 ppm (d, 1H, J=5.6 Hz); $H_2$: 9.64 ppm (d, 1H, J=9.6 Hz). *MS: (FAB, glycerol-NOBA) positive ion: $M^+$: 189 negative ion: $M^-$: 87.

Example 11

6-chloro-7-trifluoromethyl-1-methylquinolinium fluorosulphonate and 6-chloro-5-trifluoromethyl-1-methylquinolinium fluorosulphonate:

6-chloro-7-trifluoromethylquinoline and 6-chloro-5-trifluoromethylquinoline:

20 mmol of 5-amino-2-chloro-1-trifluoromethyl-benzene (ALDRICH) and 14 mmol of arsenic oxide (ALDRICH) are introduced into 80 ml of anhydrous glycerol (SIGMA), in a 100 ml three-necked round-bottomed flask, provided with stirring and a thermometer. 2.15 ml of concentrated sulphuric acid (d=1.84) are added dropwise, at room temperature. The reaction mixture is placed under vacuum [2666 Pa (20 mm of Hg)], while the temperature is gradually brought to 110° C. The stirring is maintained at this temperature for 4 hours. Then the reaction mixture is returned to atmospheric pressure, and a second addition of concentrated sulphuric acid (d=1.84; 1 ml) is made. The removal of water is then resumed, with vigorous stirring, for 4 hours under vacuum [2666 Pa (20 mm of Hg)] and a temperature never exceeding 120° C. After the reaction medium has returned to a temperature of 100° C., 50 ml of water are slowly added. The resulting solution, which has returned to room temperature and whose pH is rendered basic by addition of a concentrated ammonium hydroxide solution (d=0.89; 5 ml; PROLABO), is extracted with ethyl acetate (2×100 ml). The organic phases are combined, dried over magnesium sulphate and then the solvent is evaporated under vacuum. The solid residue is finally chromatographed on a Geduran® silica column [MERCK; 40–63 µm (200–400 mesh)] by means of an eluent mixture: methylene chloride/pentane (4/1). 6-chloro-7-trifluoromethylquinoline: yield=24%.

Physical characteristics: *m.p.=137°–139° C. *$^1$H NMR (200 MHz, CDCl$_3$) H$_3$: 7.53 ppm (dd, 1H, J=4.18–8.40 Hz); H$_5$: 7.96 ppm (s, 1H); H$_4$: 8.12 ppm (d, 1H, J=7.40 Hz); H$_8$: 8.48 ppm (s, 1H); H$_2$: 8.99 ppm (dd, 1H, J=1.38–2.78 Hz). *MS: (EI, 70eV): 233(30); 231(100); 212(10); 196(20). 6-Chloro-5-trifluoromethylquinoline : yield =8%.

Physical characteristics: *$^1$H NMR (200 MHz, CDCl$_3$): H$_3$: 7.40 ppm (dd, 1H, J=4.20–8.96 Hz); H$_7$: 7.58 ppm (d, 1H, J=9.16 Hz); H$_8$: 8.03 ppm (d, 1H, J=8.94 Hz); H$_4$: 8.45 ppm (d, 1H, J=9.00 Hz); H$_2$: 8.85 ppm (d, 1H, J=2.94 Hz). *MS: (EI, 70eV): 233(30); 231(100); 212(10); 196(20); 179(15).

6-Chloro-5-trifluoromethyl-1-methylquinolinium fluorosulphonate (BXT03071):

0.6 mmol of 6-chloro-5-trifluoromethylquinoline is introduced into 5 ml of ethylene glycol dimethyl ether, followed dropwise, with stirring, by 0.2 ml (2.4 mmol) of methylfluorosulphonate (ALFA), in a 50 ml round-bottomed flask, provided with stirring and under a nitrogen stream. After heating for 1 hour at 50° C. and then returning to room temperature the resulting solution is supplemented with 10 ml of ethyl ether. The precipitate formed is filtered, washed with ethyl ether (2×5 ml) and then dried in a vacuum oven, at 40° C., over phosphoric anhydride.

The desired product (white powder) is isolated with a yield of 72%.

Physical characteristics: *m.p.=149°–151° C. *$^1$H NMR (200 MHz, CD$_3$SOCD$_3$ : CH$_3$—N$^+$: 4.70 ppm (s, 3H); H$_3$: 8.35 ppm (dd, 1H, J=5.78–9.12 Hz); H$_7$: 8.51 ppm (d, 1H, J=9.8 Hz); H$_8$: 8.86 ppm (d, 1H, J=9.9 Hz), H$_4$: 9.38 ppm (d, 1H, J=9.06 Hz); H$_2$: 9.64 ppm (d, 1H, J=5.48 Hz). *MS: (FAB, glycerol-NOBA) positive ion: M$^+$: 345 negative ion: M$^-$: 99. 6-chloro-7-trifluoromethyl-1-methylquinolinium fluorosulphonate (BXT03072) :

The procedure used for the production of this compound is identical to that for the preceding compound, replacing 6-chloro-5-trifluoromethylquinoline with 6-chloro-7-trifluoromethylquinoline. The desired product is obtained with a yield of 80%.

Physical characteristics: *m.p.=187°–189° C. *$^1$H NMR (200 MHz), CD$_3$SOCD$_3$: CH$_3$—N$^+$: 4.78 ppm (s, 3H); H$_3$: 8.38 ppm (dd, 1H, J=6.0–9.3 Hz); H$_5$: 8.90 ppm (d, 1H); H$_8$: 8.98 ppm (s, 1H); H$_4$: 9.25 ppm (d, 1H, J=7.5 Hz); H$_2$: 9.64 ppm (d, 1H, J=7.0 Hz) . *MS: (FAB, glycerol-NOBA) positive ion: M$^+$: 345 negative ion: M$^+$: 99.

II. EXAMPLES OF APPLICATIONS

The procedures described below are examples of applications of the process according to the invention to the assay of non-protein mercaptans and reduced glutathione in an erythrocytic lysate, by means of the reagent BXT03015.

An example of reagent box is described below. This reagent box or kit according to the invention should be stored at a temperature between 0° and 4° C.

Description of the reagents

T: 50 mM phosphate buffer, pH=7.3, containing 1 mM DTPA. (It is left to equilibrate in the air and at 25° C. before use).

S1: 5% metaphosphoric acid solution. (Should be maintained between 0° and 4° C. for the preparation of the sample).

S2: 30% sodium hydroxide solution. (It is left to equilibrate in the air and at 25° C.).

R1: BXT reagent in solid form. (A 10$^{-2}$M stock solution is prepared immediately before use in T buffer).

E:GSH in solid form.

Preparation of the sample:

2 ml of whole blood is centrifuged at 4° C. and 3000 rpm for 10 minutes;

the supernatant is removed;

the erythrocytic pellet is taken up in 4 times its volume of S1 solution cooled to between 0° and 4° C.;

the suspension is mixed;

it is centrifuged at 4° C. and 3000 rpm for 10 minutes.

The supernatant thus obtained corresponding to an erythrocytic lysate, whose proteins have been precipitated, diluted ⅕, will constitute the sample to be assayed (it should be maintained between 0° and 4° C. for the measurements).

1. Assay of total mercaptans:

Assay procedure:

The measurements are carried out at 25° C. in a spectrophotometer whose measurement cuvettes are thermostated.

The reaction mixture corresponding to each assay is prepared immediately before use according to the following procedure, for 1 ml cuvettes:

the following are mixed: 1100 µl of sample to be assayed and 800 µl of T solution;

the mixture is left to incubate for 1 minute at 25° C.;

the reaction is started by adding 100 µl of 10$^{-2}$M R1 stock solution in T buffer; and the mixture is left to incubate for 5 minutes at 25° C.

The measurement of absorbance (A) is carried out at 356 nm in the case where R1 is the compound BXT03015, in cuvettes with an optical path length of 1 cm, against the air.

The GSH present in the reagent box (E) can be used to define a calibration curve, if necessary.

Expression of the results:

Under the conditions of this assay, the concentration of total mercaptans is determined according to the formula:

[total mercaptans]=(A/16200)×50 in which A is the absorbance measured. Remark: The molar extinction coefficient used here (16200 1.mol$^{-1}$cm$^{-1}$) is a mean of the molar extinction coefficients at 356 nm which are obtained for the adducts formed between the reagent BXT03015 and the main physiologically important mercaptans described in Table I above. The relative error is equal, under these conditions, to ±9%.

In this case, a measurement of the concentration of total mercaptans in the sample is obtained, expressed in moles/1.

2. Assay of reduced glutathione:

Assay procedure:

The measurements are carried out at 25° C. in a spectrophotometer whose measurement cuvettes are thermostated.

A reaction mixture corresponding to each assay is prepared immediately before use according to the following procedure, for 1 ml cuvettes:

50 µl of solution S2 are added to the solution which served to assay the total mercaptans; and the mixture is left to incubate for 15 minutes at 25° C.

The measurement of absorbance is carried out at 400 nm in the case where R1 is the compound BXT03015, in cuvettes with an optical path length of 1 cm, against the air.

Expression of the results:

Under the conditions of this assay, the concentration of GSH is determined according to the formula:

$$[GSH] = (A'/14700) \times 50$$

in which A' represents the absorbance measured.

In this case, a measurement of the concentration of reduced glutathione (GSH) is obtained, expressed in moles/1.

A solution of GSH (reagent E) at $10^{-2}$ mole/1 in 5% metaphosphoric acid (solution S1) can be prepared immediately before use and serve for a calibration curve, if necessary.

REFERENCES

1—DOLPHIN D., POULSON R. and AVRAMOVIC O. Eds. (1989) Glutathione: chemical, biochemical and medical aspects, Vols. I & II, J. WILEY and Sons 2—ANDERSON M. E. (1989) in DOLPHIN D., POULSON R. and AVRAMOVIC O. Eds., Glutathione: chemical, biochemical and medical aspects, Vols. I & II, J. WILEY and Sons, pp. 339–365

3—TIETZE F. (1969) Anal. Biochem., 27, 502–522

4—LING. B. LIN, DEWAELE C., BAEYENS W. R. G. (1991) J. Chromatogr., 553(1–2), 433–9

5—SOFIC E., RIEDERER P., BURGER R., GSELL W., HEUSCHNEIDER G. (1991) Fresenius. J. Anal. Chem., 339, 258–260

6—ELLMAN G. L. (1959) Arch. Biochem. Biophys., 82, 70–77

7—SEDLAK J. and LINDSAY R. H. (1968) Anal. Biochem., 25, 192–205

8—LUTHRA N. P., DUNLAP B. and ODAM J. D. (1981) Anal. Biochem., 117 94–102

9—TORSHINSKI Y. M. (1981) Sulfur in Proteins, Pergamon Press, pp. 124–125

10—FARISS M. W. and REED D. J. (1987) Meth. in Enzymol., 143, 101–109

11—REED D. J. and BEATTY P. W. (1980) Reviews in Biochemical Toxicology—Elsevier, 2, 213–24

12—KOSOWER E. M., KOSOWER N. S. and RADKOWSKY A. (1983), in the Functions of Glutathione: biochemical, physiological, toxicological and clinical aspects, LARSSON A. et al. Eds., Raven press, New York, pp. 243–250

13—RICE G. C., BUMP E. A., SHRIEVE D. C., LEE W. and KOVACS M. (1986) Cancer Res., 46, 6105–5110.

14—HOLLOWAY C. J. (1987) J. of Chromatogr., 390, 101–110

15—MUTUS B., WAGNER J. D., TALPAS C. J., DIMMOCK J. R., PHILLIPS O. A., REID R. S. (1989) Anal. Biochem., 177, 237–243

16—GRIFFITH O. W. (1980) Anal. Biochem., 106, 207–212

17—HISSIN P., HILF R. (1976) Anal. Biochem., 74, 214–226

18—MARTENSSON J. (1987) J. of Chromatogr., 420, 152–157

19—FAHEY R. C. (1989), in "Glutathione: chemical, biochemical and medical aspects", DOLPHIN D., POULSON R., AVRAMOVIC O. Eds., John Wiley and Sons, pp. 303–337

20—BN LING B., BAEYENS F. R. G., MARYSAEL H. (1989) Anal. Chim. Acta, 227, 203–209

21—INOUE M., SAITO Y., HIRATA E., MORINO Y., NAGASE S., (1987) J. Prot. Chem., 6, 207–225

We claim:

1. A process for assaying total mercaptans in an aqueous sample comprising the steps of:

a) adding to the sample to be assayed, buffered within the pH range of 7.0 to 7.5, an aliquot of a stock solution, in water or a water-miscible solvent, of a reagent of general formula I wherein:

$R^1$ is selected from the croup consisting of a $C_1$–$C_6$ alkyl, benzyl, p-nitrobenzyl and o,p-dinitrophenyl;

$R^2$ is selected from the group consisting of hydrogen and methyl;

$R^3$ is selected form the group consisting of hydrogen, halogen and SCN;

$R^4$ is selected from the group consisting of hydrogen, halogen $NO_2$ and $CF_3$;

$R^5$ is selected from the group consisting of hydrogen, $NO_2$ and halogen;

$R_6$ is selected from the group consisting of hydrogen, halogen, $NO_2$ and $CF_3$;

$R^7$ is selected from the group consisting of hydrogen, hydroxy, benzyloxy and $NO_2$;

Y is selected from the group consisting of halogen, methyl sulphate, fluorosulphonate, phosphate, tetrafluoroborate and tosylate, in excess, b) homogenizing the reaction medium thus obtained, c) leaving to incubate for at least 5 minutes, d) measuring the absorbance of the substitution products or adducts formed between the reagent and the mercaptans present in the sample and e) determining the concentration, in moles/liter of total mercaptans present in the sample, according to the formula:

total mercaptans=$(A/\epsilon m \times d) \times D$ in which:

A represents the absorbance measured, εm represents the specific molar extinction coefficient for the reagent used, expressed in 1 mole$^{-1}$–cm$^{-1}$, d represents the cuvette length, expressed in cm, and d represents the coefficient of dilution.

2. Process according to claim 1, wherein the reagent used is the reagent 4-chloro-7-trifluoromethyl-1-methyl-quinolinium tetrafluoroborate.

3. The process according to claim 1 wherein the aqueous sample is a biological sample.

4. The process of claim 1, wherein the absorbance is measured by means of a spectrophotometer at 400 nm.

5. The process of claim 1, wherein at least one of $R^3$, $R^4$ and $R^6$ is halogen.

6. Process for assaying reduced gluthatione, GSH, in an aqueous sample, comprising the steps of:

a) adding to the sample to be assayed, buffered within the pH range of 7.0 to 7.5, an aliquot of a stock solution, in water or in a water-miscible solvent, of a reagent of general formula I wherein:

$R^1$ is selected from the group consisting of a $C_1$–$C_6$ alkyl, benzyl, p-nitrobenzyl and o,p-dinitrophenyl;

$R^2$ is selected from the group consisting of hydrogen and methyl;

$R^3$ is selected form the group consisting of hydrogen, halogen and SCN;

$R^4$ is selected from the group consisting of hydrogen, halogen, $NO_2$ and $CF_3$;

$R^5$ is selected from the group consisting of hydrogen, $NO_2$ and halogen;

$R_6$ is selected from the group consisting of hydrogen, halogen, $NO_2$ and $CF_3$;

$R^7$ is selected from the group consisting of hydrogen, hydroxy, benzyloxy and $NO_2$;

Y is selected from the group consisting of halogen, methyl sulphate, fluorosulphonate, phosphate, tetrafluoroborate and tosylate, in excess, b) homogenizing the reaction medium thus obtained, c) leaving to incubate for at least 5 minutes, d) adjusting the pH of the mixture to a value of between 12.8 and 13.8, according to the reagent chosen, e) leaving to incubate for at least 15 minutes, f) measuring, by means of a spectrophotometer, the absorbance of the chromophoric thione produced by β-elimination, specifically with the adduct GSH reagent and g) determining the concentration moles/liter of GSH in the sample, according to the formula:

GSH=(A'/εm×d)×D in which:

A' represents the absorbance measured,

εm represents the specific coefficient of molar extinction of the reagent used, expressed in 1 mole$^{-1}$ cm$^{-1}$, d represents the cuvette length, expressed in cm, and D represents the coefficient of dilution.

7. The process of claim 6, further comprising after step c), the supplemental steps of:

c.1) measuring the absorbance of the substitution products or adducts formed between the reagent and the mercaptans present in the sample.

c.2) determining the concentration, in moles/liter, of total mercaptans present in the sample according to the formula:

total mercaptans=A/εm×d)×D in which:

A represents the absorbance measured;

εm; d; D are defined in claim 6; and c.3) assaying the concentration of mercaptans distinct from reduced glutathione GSH in said aqueous sample by substracting the concentration of total mercaptans from the concentration of GSH.

8. The process according to claim 7 wherein the aqueous sample is a biological sample.

9. The process according to claim 6 wherein the aqueous sample is a biological sample.

10. The process of claim 6, wherein said reagent is 4-chloro-7-trifluoromethyl-1-methylquinolinium tetrafluoroborate.

11. The process of claim 6, wherein the absorbance is measured by means of a spectrophotometer 400 nm.

12. The process of claim 6, wherein at least one of $R^3$, $R^4$ and $R^6$ is halogen.

13. A set or kit for assaying mercaptans including reduced glutathione (GSH) in an aqueous sample comprising:

(a) a reagent constituted by a quinolinium compound having the general formula I:

wherein:

$R^1$ is selected from the group consisting of a $C_1$–$C_6$ alkyl, benzyl, p-nitrobenzyl and o,p-dinitrophenyl;

$R^2$ is selected from the proud consisting of hydrogen and methyl;

$R^3$ is selected form the group consisting of hydrogen, halogen and SCN;

$R^4$ is selected from the group consisting of hydrogen, halogen, $NO_2$ and $CF_3$;

$R^5$ is selected from the group consisting of hydrogen, $NO_2$ and halogen;

$R_6$ is selected from the group consisting of hydrogen, halogen, $NO_2$ and $CF_3$;

$R^7$ is selected from the group consisting of hydrogen, hvdroxy, benzyloxy and $NO_2$;

Y is selected from the group consisting of halogen, methyl sulphate, fluorosulphonate, phosphate, tetrafluoroborate and tosylate and wherein at least one of $R^3$, $R^4$, and $R^6$ is halogen and wherein at least one of $R^3$ to $R^7$ is other than hydrogen, halogen or nitro,

(b) a medium in an amount sufficient to bring the aqueous sample to an alkaline pH.

14. The kit of claim 13, further comprising a buffer in an amount sufficient to bring the pH of said aqueous sample between 7.0 and 7.5.

15. The kit of claim 13, wherein said reagent is 4-chloro-7-trifluoromethyl-1-methylquinolinium tetrafluoroborate.

16. The kit of claim 13, wherein $R^4$ is a halogen.

17. A process for assaying reduced glutathione (GSH) in an aqueous sample comprising the following steps:
(a) forming a chromophoric substitution product by reacting the mercaptans present in the sample with a reagent constituted by a quinolinium compound having the general formula I:

wherein:
$R^1$ is selected from the group consisting of a $C_1$–$C_6$ alkyl, benzyl, p-nitrobenzyl and o,p-dinitrophenyl;
$R^2$ is selected from the group consisting of hydrogen and methyl;
$R^3$ is selected form the group consisting of hydrogen, halogen and SCN;
$R^4$ is selected from the group consisting of hydrogen, halogen, $NO_2$ and $CF_3$;
$R^5$ is selected from the group consisting of hydrogen, $NO_2$ and halogen;
$R_6$ is selected from the group consisting of hydrogen, halogen, $NO_2$ and $CF_3$;
$R^7$ is selected from the group consisting of hydrogen, hydroxy, benzyloxy and $NO_2$;
Y is selected from the group consisting of halogen, methyl sulphate, fluorosulphonate, phosphate, tetrafluoroborate and tosylate.
(b) bringing the aqueous sample to an alkaline pH to form a specifically chromophoric thione from the chromophoric substitution product formed in step (a), between GSH and said reagent; and
(c) measuring the absorbance of the chromophoric thione, said absorbance providing information about the concentration in reduced glutathione in said aqueous sample.

18. The process of claim 17, further comprising after step c), the supplemental steps of:
c.1) measuring the absorbance of the substitution products or adduct formed between the reagent and the mercaptans present in the sample,
c.2) determining the concentration, in mol/liter, of total mercaptans present in the samples according to the formula:

total mercaptans=A/(∈m×d)×D in which:
A represents the absorbance measured;
∈m; d; D are defined in claim 17; and
c.3) assaying the concentration of mercaptans distinct from reduced glutathione GSH in said aqueous sample by subtracting the concentration of total mercaptans from the concentration of GSH.

19. The process according to claim 17 wherein the aqueous sample is a biological sample.

20. The process according to claim 19 wherein the biological sample is selected from a group consisting of erythrocytes, plasma and blood platelets.

21. The process according to claim 17 wherein the absorbance is measured by means of a spectrophotometer at 400 nm.

22. The process of claim 17, wherein said reagent is 4-chloro-7-trifluoromethyl-1-methylquinolinium tetrafluoroborate.

23. The process of claim 17, wherein at least one of $R^3$, $R^4$ and $R^6$ is halogen.

24. A process for assaying reduced glutathione (GSH) in an aqueous sample comprising the following steps:
(a) forming a chromophoric substitution product by reacting the mercaptans present in the sample with a reagent constituted by a quinolinium compound having the general formula I:

wherein:
$R^1$ is selected from the group consisting of a $C_1$–$C_6$-alkyl, benzyl, p-nitrobenzyl and o,p-dinitrophenyl;
$R^2$ is selected from the group consisting of hydrogen and methyl;
$R^3$ is selected from the group consisting of hydrogen, F, Cl, Br, I and SCN;
$R^4$ is selected from the group consisting of hydrogen, F, Cl, $NO_2$ and Cl;
$R^5$ is selected from the group consisting of hydrogen, $NO_2$ and Cl;
$R^6$ is selected from the group consisting of F, Cl, $NO_2$ and $CF_3$;
$R^7$ is selected from the group consisting of hydrogen, benzyloxy and $NO_2$;
Y is selected from the group consisting of halogen, methyl sulphate, fluorosulphonate, phosphate, tetrafluoroborate and tosylate.
(b) bringing the aqueous sample to an alkaline pH ranging between 12.8 and 13.8 to form a specifically chromophoric thione from the chromophoric substitution product formed in step (a), between GSH and said reagent; and
(c) measuring the absorbance of the chromophoric thione, said absorbance providing information about the concentration of reduced glutathione in said aqueous sample.

25. The process according to claim 24 wherein the aqueous sample is a biological sample.

26. The process according to claim 24 wherein the absorbance is measured by means of a spectrophotometer at 400 nm.

27. The process of claim 24, further comprising after step c), the supplemental steps of:
c.1) measuring the absorbance of the substitution products or adducts formed between the reagent and the mercaptans present in the sample,
c.2) determining the concentration, in mols/liter, of total mercaptans present in the samples according to the formula:

total mercaptans=A/(∈m×d)×D in which:

A represents the absorbance measured;
εm; d; D are as defined in claim 24; and
c.3) assaying the concentration of mercaptans distinct from reduced glutathione GSH in said aqueous sample by subtracting the concentration of total mercaptans from the concentration of GSH.

28. The process of claim 24, wherein said reagent is 4-chloro-7-trifluoromethyl-1-methylquinolinium tetrafluoroborate.

29. The process of claim 24, wherein at least one of $R^3$, $R^4$ and $R^6$ is halogen.

30. A process for assaying total mercaptans in an aqueous sample, comprising the steps of:
(a) forming a chromophoric substitution product by reacting the mercaptans present in the sample reagent constituted by a quinolinium compound in the general formula I:

wherein:
$R^1$ is selected form the group consisting of a $C_1$–$C_6$-alkyl, benzyl, p-nitrobenzyl and o,p-dinitrophenyl;
$R^2$ is selected from the group consisting of hydrogen and methyl;
$R^3$ is selected from the group consisting of hydrogen, halogen and SCN;
$R^4$ is selected from the group consisting of hydrogen, $NO_2$ and $CF_3$;
$R^5$ is selected from the group consisting of hydrogen, $NO_2$ and Cl;
$R^6$ is selected from the group consisting of hydrogen, halogen, $NO_2$ and $CF_3$;
$R^7$ is selected from the group consisting of hydrogen, hydroxy, benzyloxy and $NO_2$;
Y is selected from the group consisting of halogen, methyl sulphate, fluorosulphonate, phosphate, tetrafluoroborate and tosylate, and
(b) measuring the absorbance of the chromophoric substitution product, said absorbance providing information about the concentration of total mercaptans present in said aqueous sample.

31. The process of claim 30, wherein said reagent is 4-chloro-7-trifluoromethyl-1-methylquinolinium tetrafluoroborate.

32. The process of claim 30, wherein at least one of $R^3$, $R^4$ and $R^6$ is halogen.

33. The process according to claim 30 wherein the absorbance is measured by means of a spectrophotometer at 400 nm.

34. A set or kit for assaying mercaptans including reduced glutathione GSH in an aqueous sample comprising:
a) a reagent constituted by 4-chloro-7-trifluoromethyl-1-methylquinolinium tetrafluoroborate;
b) a medium in an amount sufficient to bring the aqueous sample to an alkaline pH.

35. A set or Kit for assaying mercaptans including reduced glutathione (GSH) in an aqueous sample comprising:
a) a reagent selected from the group consisting of 4-chloro-1,2-dimethylquinolinium tetrafluoroborate, 7-chloro-1,2-dimethylquinolinium tetrafluoroborate, 5-chloro-8-hydroxy-1-methylquinolinium tetrafluoroborate, 5-chloro-8-benzyloxy-1-methylquinolinium tetrafluoroborate, 5-fluoro-8-nitro-1-methylquinolinium fluorosulfonate, 6-chloro-7-trifluoromethyl-1-methylquinolinium fluorosulfonate, and 6-chloro-5-trifluoromethyl-1-methylquinolinium fluorosulfonate;
b) a medium in an amount sufficient to bring the aqueous sample to an alkaline pH.

* * * * *